United States Patent [19]

Förster

[11] 4,292,025
[45] Sep. 29, 1981

[54] ORTHODONTIC DEVICE FOR ROTATING A TOOTH

[75] Inventor: Rolf Förster, Pforzheim, Fed. Rep. of Germany

[73] Assignee: Bernhard Förster GmbH, Pforzheim, Fed. Rep. of Germany

[21] Appl. No.: 157,388

[22] Filed: Jun. 9, 1980

[30] Foreign Application Priority Data

Jun. 7, 1979 [DE] Fed. Rep. of Germany ... 791639[U]

[51] Int. Cl.³ .............................................. A61C 7/00
[52] U.S. Cl. ................................................... 433/18
[58] Field of Search ........................... 433/7, 6, 18, 21

[56] References Cited

U.S. PATENT DOCUMENTS

| | | | |
|---|---|---|---|
| 2,266,860 | 12/1941 | Griesinger | 433/7 |
| 3,529,353 | 9/1970 | Schiaroli | 433/7 |
| 4,026,023 | 5/1977 | Fisher | 433/7 |
| 4,202,328 | 5/1980 | Sukkarie | 433/18 |

Primary Examiner—Robert Peshock
Attorney, Agent, or Firm—Balogh, Osann, Kramer, Dvorak, Genova & Traub

[57] ABSTRACT

A wire loop adapted to be slung around a tooth to be rotated has two end portions which respectively extend through and are guided by two juxtaposed spaced apart through holes formed in a body. Polygonal roller means are rotatably mounted in said body between said holes and have radially outer edge portions. Said holes are laterally open toward said roller means to expose said wire end portions in said holes to said radially outer edge portions, which bite into the sides of said wire end portions in said holes. Said roller means are rotatable to move said wire end portions in said holes by means of said radially outer edge portions biting into said wire end portions.

9 Claims, 6 Drawing Figures

ORTHODONTIC DEVICE FOR ROTATING A TOOTH

This invention relates to an orthodontic device for rotating a tooth in the upper or lower jaw.

It is known to correct twisted teeth by means of removable devices which comprise protruding springs, leaf springs or spreading devices. These elements have the disadvantage that they do not physically embrace the twisted tooth but engage the same only at one point so that it is not possible to easily effect a desired rotation of the individual tooth although this is sometimes necessary.

It is an object of the invention to provide means for a controlled rotation also of individual teeth.

The orthodontic device for a correction of teeth in the upper or lower jaw is provided with a wire loop, which is slung around the tooth to be rotated and extends at both ends through a body, in which a substantially cylindrical or polygonal roller is rotatably mounted and bites into the sides of the wire and is rotatable to pull and push the wire loop so that an individual tooth which is fully embraced by the wire loop can be individually rotated.

Centrally between the holes formed in the body and serving to guide the wire end portions, a polygonal roller may be rotatably mounted in the body and may have radially or peripheral outer edges which like gear teeth bite into the sides of the wire. As a result, uniform tensile and compressive forces are exerted on opposite sides of the tooth to be rotated. Alternatively, two juxtaposed polygonal rollers may be rotatably mounted in the body between the holes for guiding the wire ends. Each of said rollers has radially or peripheral outer edge portions biting like gear teeth into one side of the adjacent wire. In that case, different tensile and compressive forces acting on the tooth can be adjusted.

Further details of an orthodontic device according to the invention are apparent from the following description of two preferred embodiments shown on the drawings, in which.

Figure 1:
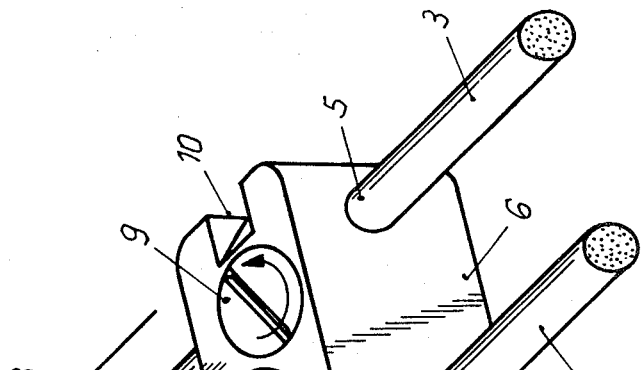
FIG. 1 is a perspective view showing a first embodiment.

As is apparent from the drawing, the orthodontic device for rotating individual teeth of the upper jaw or lower jaw comprises a wire loop 1, formed as a single integral unit, and which is slung or placed around the tooth Z to be twisted and has two end portions 2 and 3, which extend through and are guided in holes 4 and 5 of a body 6. In the embodiment shown in FIGS. 1 to 3, two substantially cylindrical or polygonal rollers 7 are rotatably mounted in the body 6 by a rivetable stub axle 8 and a slotted head 9 rollers 7 are positioned in body 6, perpendicularly to and between holes 4 and 5. Each of the holes 4 and 5 is laterally open toward the adjacent roller 7. Each roller 7 has outer edge portions, which consist of a material that is harder than that of the wire end portions 2 and 3 and which like gear teeth bite into the sides of the wire end portions 2 and 3 so that the loop 1 can be adjusted to effect a rotation of the tooth Z.

Figure 6:
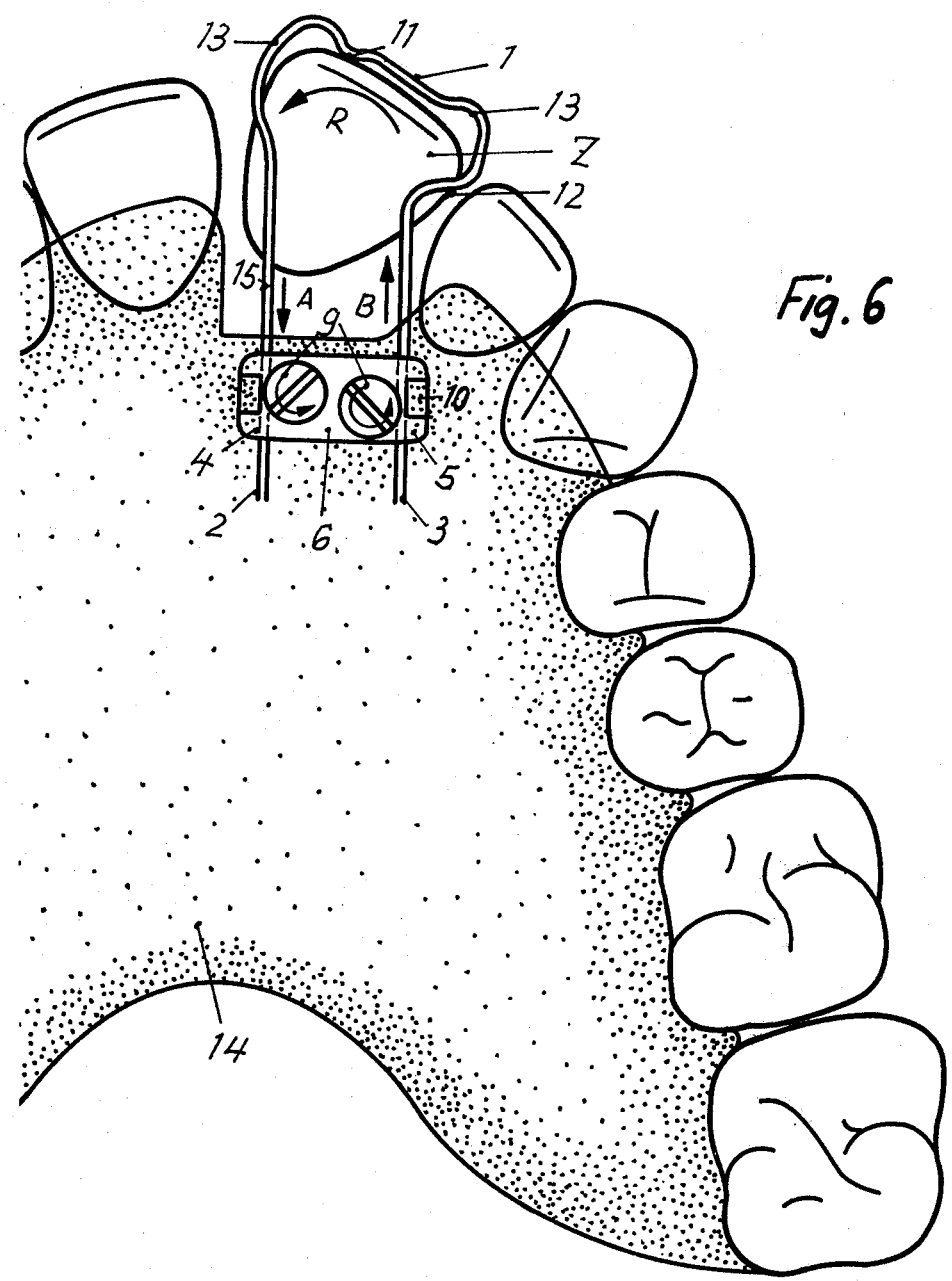
FIG. 6 is a top plan view of an orthodontic appliance as shown in FIGS. 1 to 3 installed on the upper jaw.

The body 6 is formed with inclined grooves 10 for anchoring the body in the mounting or base plate 14, as shown in FIG. 6. When tension in the direction indicated by the arrow A is exerted on the tooth-engaging portion 11 of the wire loop 1 and pressure in the direction indicated by the arrow B is applied to the tooth-engaging portion 12 of the wire loop, the tooth can be rotated in the sense indicated by the arrow R. The wire loop 1 has bulges 13 for adapting the wire loop 1 to the tooth Z.

Figure 4:
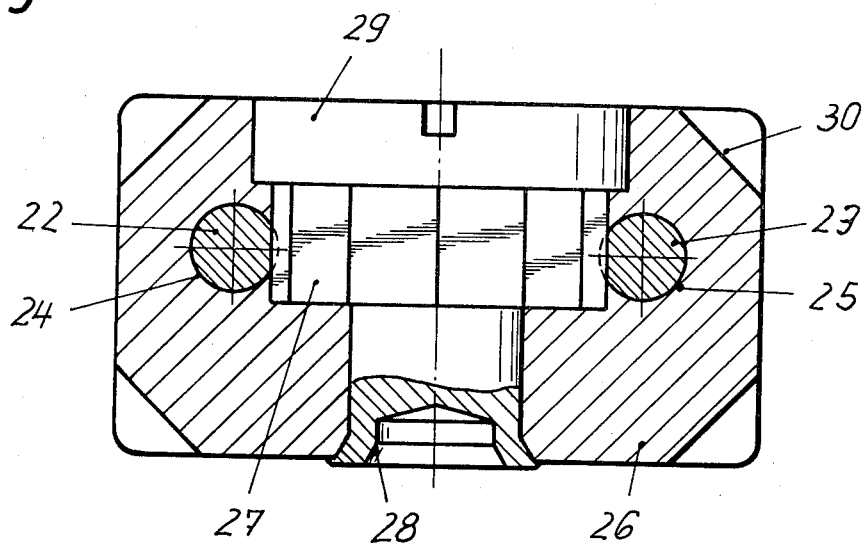
FIGS. 4 and 5 are a side elevation and a top plan view, respectively, showing a second embodiment, partly cut open.
Figure 5:
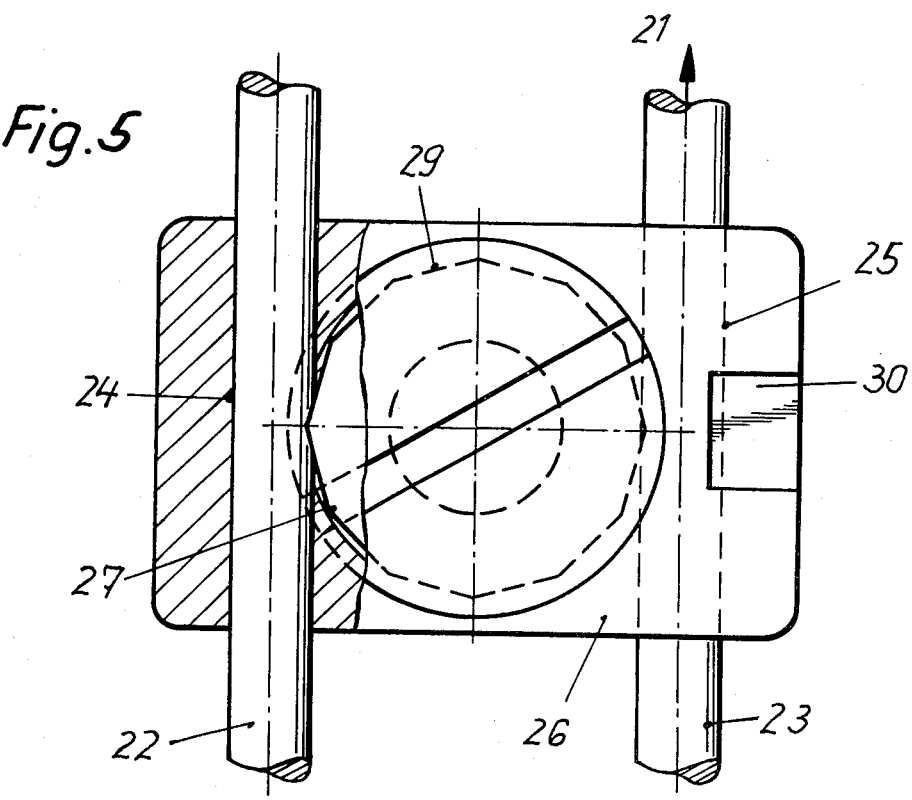

The device shown in FIGS. 4 and 5 comprises a body 26 having holes 24 and 25, in which the end portions 22 and 23 of the wire loop 21 are guided. A substantially cylindrical or polygonal roller 27 is rotatably mounted in the body 26 by means of a rivetable stub axle 28 and a slotted head 29 and has radially or peripheral outer edge portions which on both sides bite like gear teeth into the wire end portions, as is shown in FIG. 5.

The body 26 is also formed with anchoring grooves 30. Because there is only one polygonal roller 27, the tensile and compressive forces exerted on the wire loop 21 will be equal in magnitude. In the first embodiment, shown in FIGS. 1 to 3, the provision of two polygonal rollers 27 permits of exerting a tensile force (arrow A) and a compressive force (arrow B) which differ in magnitude.

Figure 2:
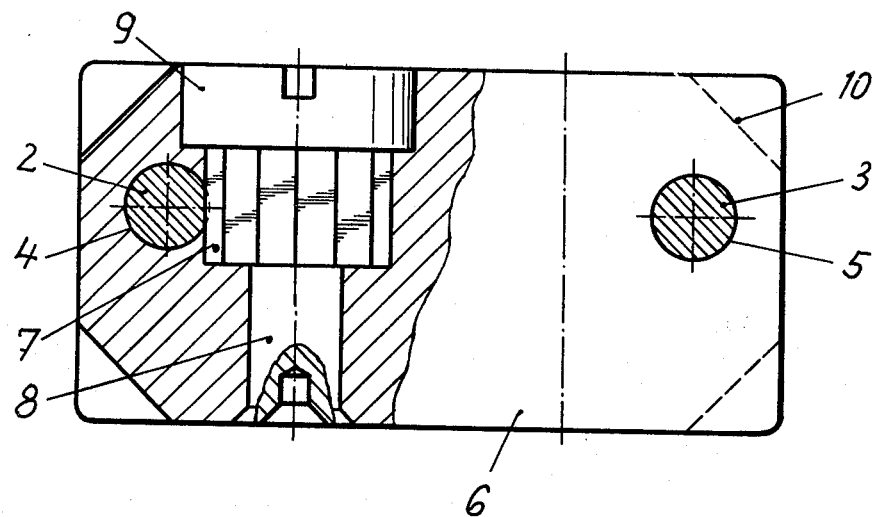
FIGS. 2 and 3 are a side elevation and a top plan view of the first embodiment, partly cut open.
Figure 3:
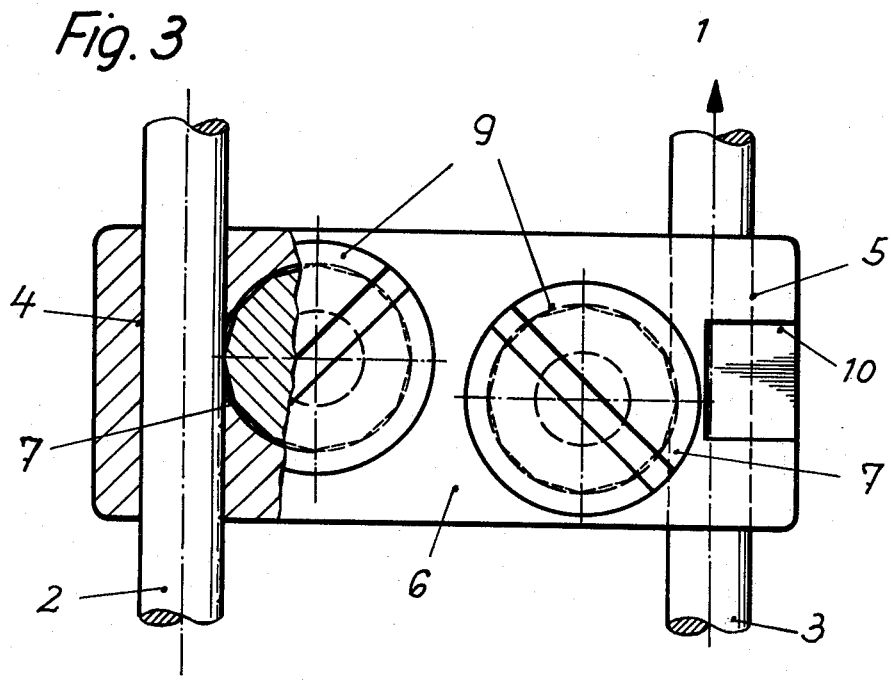

FIG. 6 shows how the embodiment of FIGS. 1 and 3 can be installed in the upper jaw. A baseplate 14 is applied to the palate and has an aperture 15 receiving the body 6, which is provided with the wire loop 1 for rotating the tooth Z in the direction indicated by the arrow R. Further details have already been described hereinbefore.

What is claimed is:

1. An orthodontic device for rotating a tooth comprising:
   a base plate having an aperture, a body secured to said base plate and received in the aperture thereof, said body having two juxteposed, spaced apart through holes,
   cylindrical roller means rotatably mounted in said body, and positioned perpendicularly to and between said holes, and
   an integrally formed wire loop which is adapted to be disposed around a tooth to be rotated, and which has two wire end portions extending through said body, respectively traversing and being guided in said holes,
   said roller means having outer edge portions biting into the sides of said wire end portions in said holes,
   said holes being laterally open toward said roller means to expose said wire end portions to said outer edge portions,
   said roller means being rotatable to move said wire end portions in said holes by means of said outer edge portions so as to effect rotation of the tooth.

2. An orthodontic device as set forth in claim 1, in which said outer edge portions consist of a material which is harder than the material of said wire end portions.

3. An orthodontic device as set forth in claim 1, in which
   said roller means consist of a single polygonal roller, which is rotatably mounted in said body centrally between said holes and is formed with said outer edge portions on opposite sides and said outer edge portions on opposite sides of said single roller bite into respective ones of said wire end portions.

4. An orthodontic device as set forth in claim 1, in which said roller means comprises at least one polygonal roller, which is rotatably mounted in said body by means of a rivetable stub axle at one end of said roller and a slotted head at the other end of said roller.

5. An orthodontic device as set forth in claim 1, in which said wire loop has curved portions for engaging the tooth that is to be rotated.

6. An orthodontic device as set forth in claim 6, in which said wire loop has bulges for the adaptation of said loop to said tooth.

7. An orthodontic device as set forth in Claim 1, in which said body has anchoring grooves.

8. An orthodontic device as set forth in claim 8, in which said anchoring grooves are oblique and provided on opposite sides of said body.

9. An orthodontic device for rotating a tooth by means of a wire loop which is slung around said tooth and has two wire end portions, comprising a body having two juxtaposed, spaced apart holes adapted to respectively receive and guide said wire end portions, and polygonal roller means which are rotatably mounted in said body between said holes and have radially outer edge portions, said holes being laterally open toward said roller means and adapted to expose said wire end portions in said holes to said radially outer edge portions, said radially outer edge portions being adapted to bite into the sides of said wire end portions in said holes, said roller means being rotatable to move said wire end portions in said holes by means of said radially outer edge portions biting into said wire end portions.

* * * * *